(12) United States Patent
Vrabec

(10) Patent No.: US 10,105,371 B2
(45) Date of Patent: Oct. 23, 2018

(54) USE OF MEDICATIONS WITH NEUROPROTECTIVE PROPERTIES TO PREVENT OR REDUCE THE RISK OF ISCHEMIA-REPERFUSION INJURY IN A SUBJECT

(71) Applicant: Tamara Vrabec, Danville, PA (US)

(72) Inventor: Tamara Vrabec, Danville, PA (US)

(*) Notice: Subject to any disclaimer, the term of this patent is extended or adjusted under 35 U.S.C. 154(b) by 0 days.

(21) Appl. No.: 15/193,625

(22) Filed: Jun. 27, 2016

(65) Prior Publication Data
US 2017/0100410 A1 Apr. 13, 2017

Related U.S. Application Data

(60) Provisional application No. 62/239,639, filed on Oct. 9, 2015.

(51) Int. Cl.
*A61K 31/5575* (2006.01)
*A61K 45/06* (2006.01)

(52) U.S. Cl.
CPC .......... *A61K 31/5575* (2013.01); *A61K 45/06* (2013.01)

(58) Field of Classification Search
CPC .......................... A61K 31/5575; A61K 45/06
See application file for complete search history.

(56) References Cited

PUBLICATIONS

Bonomi et al., "Vascular risk factors for primary open angle glaucoma: the Egna-Neumarkt Study, Ophthalmology", 107 (7):1287-1293, 2000.
Kaur et al., "Hypoxia-ischemia and retinal ganglion cell damage", ClinOphthalmol, 2(4):879-889, 2008.
Seth et al., "Assessment of optic nerve cup-to-disc ratio changes in patients receiving multiple injections of intravitreal vascular endothelial growth factor agents", Retina, 29:956-959, 2009.
Kanamori et al., "Tafluprost protects rat retinal ganglion cells from apoptosis in vitro and in vivo", Graefes Arch Clin Exp Ophthalmol, 247(10):1353-1360, 2009.
Nagata et al., "OCT evaluation of neuroprotective effects of tafluprost on retinal injury after intravitreal injection of endothelin-1 in the rat eye", Invest Ophthalmol Vis Sci, 55(2):1040-1047, 2014.
Spaide et al., "Ranibizumab according to need: a treatment for age-related macular degeneration", Am J Ophthalmol, 143(4):679-680, 2007.
Martinez-de-la-Casa et al., "Retinal Nerve Fiber Layer Thickness Changes in Patients with Age-Related Macular Degeneration Treated with Intravitreal Ranibizumab", Invest Ophthalmol Vis Sci, 53(10):6214-6218, 2012.
Sobaci et al., "Effects of multiple intravitreal anti-VEGF injections on retinal nerve fiber layer and intraocular pressure: a comparative clinical study", Int J Ophthalmol, 6(2):211-215, 2013.

Demirel et al., "The Effect of Multiple Injections of Ranibizumab on Retinal Nerve Fiber Layer Thickness in Patients with Age-Related Macular Degeneration", Curr Eye Res, 40(1):87-92, 2015.
Horsley et al., "Retinal Nerve Fiber Layer Thickness in Patients Receiving Chronic Anti-Vascular Endothelial Growth Factor Therapy", Am J Ophthalmol, 150:558-561, 2010.
Adelman et al., "Persistent Ocular Hypertension Following Intravitreal Bevacizumab and Ranibizumab Injections", J Ocular Pharmacol Ther, 26(1):105-110, 2010.
Good et al., "Sustained elevation of intraocular pressure after intravitreal injections of anti-VEGF agents", Br J Ophthalmol, 95(8):1111-1114, 2011.
Tseng et al., "Sustained Increased Intraocular Pressure Related to Intravitreal Antivascular Endothelial Growth Factor Therapy for Neovascular Age-related Macular Degeneration", J Glaucoma, 21(4):241-247, 2012.
Kim et al., "Short-term Intraocular Pressure Changes Immediately After Intravitreal Injections of Anti-Vascular Endothelial Growth Factor Agents", Am J Ophthalmol, 146(6):930-934, 2008.
Gismondi et al., "Short-term Effect of Intravitreal Injection of Ranibizumab (Lucentis) on Intraocular Pressure", J Glaucoma, 18(9):658-661, 2009.
Shih et al., "Secondary neuroprotective effects of hypotensive drugs and potential mechanisms of action", Expert Rev Ophthalmol, 7(2): 161-175, 2012.
Zengin MO et al., "Retinal nerve fiber layer thickness changes in obstructive sleep apnea syndrome: one year follow-up results", Int J Ophthalmol, 7:704-708, 2014.
Winquist et al., "Cerebral ischemia-reperfusion injury and adhesion", Neurology, 49 (Suppl 4) S23-S26, 1997.
Nishijima et al., "Vascular Endothelial Growth Factor-A Is a Survival Factor for Retinal Neurons and a Critical Neuroprotectant during the Adaptive Response to Ischemic Injury", Am J Pathol, 171:53-67, 2007.
Hale B et al., "Changes in the retinal nerve fiber layer in patients receiving intravitreal anti-VEGF agents", The Retina Society Annual Meeting, San Francisco, CA, Sep. 24, 2010, p. 141.
Kurashima et al., "Effects of prostaglandin F2a analogues on endothelin-1-induced impairment of rabbit ocular blood flow: Comparison among tafluprost, travoprost, and latanoprost", Experimental Eye Research, vol. 91, pp. 853-859, (2010).
Flammer et al., "What Is the Present Pathogenetic Concept of Glaucomatous Optic Neuropathy?", J Survophthal, 52(6): S162-S173, (2007).
Hoy, "Tafluprost/Timolol: A Review in Open-Angle Glaucoma or Ocular Hypertension", Drugs, 75(15):pp. 1807-1813, (2015).
Ichiyama et al., "Anterior Chamber Paracentesis Might Prevent Sustained Intraocular Pressure Elevation after Intravitreal Injections of Ranibizumab for Age-Related Macular Degeneration", Ophthalmic Res, 52(4):pp. 234-238 (2014).
Leung, "Detecting optic nerve head deformation and retinal nerve fiber layer thinning in glaucoma progression", Taiwan Journal of Ophthalmology, 5(2): pp. 50-55, (2015).

(Continued)

*Primary Examiner* — Sudhakar Katakam
(74) *Attorney, Agent, or Firm* — Riverside Law LLP

(57) ABSTRACT

Provided are methods for treatment and prevention of ischemia-reperfusion injury and chronic intermittent hypoxia related injury through administering a neuroprotective compound. A subject benefiting from the method of the invention may be prescribed or undergoing anti-VEGF treatment, for example an IVAV treatment regimen, or may be diagnosed with a disorder such as sleep apnea.

9 Claims, 4 Drawing Sheets

(56) References Cited

PUBLICATIONS

Liu et al., "Tafluprost once daily for treatment of elevated intraocular pressure in patients with open-angle glaucoma", Clinical Ophthalmology, 7: pp. 7-14, (2013).
Matsuura et al., "Stimulatory Interaction Between Vascular Endothelial Growth Factor and Endothelin-I on Each Gene Expression", Hypertension, 32(1): pp. 89-95, (1998).
Stephenson, "Glaucoma Medications: It's All in the Delivery", Review of Ophthalmology, pp. 1-13 (2014). (https://www.reviewofophthalmology.com/article/glaucoma-medications-its-all-in-the-delivery).
Vasudevan et al., "Neuroprotection in glaucoma", Indian J Ophthalmol, 59(Suppl. 1): pp. S102-S113, (2011).

| | Group 1<br>Paracentesis<br>(n=75) | Group 2<br>No Paracentesis<br>(n=104) | Group 3<br>Control<br>(n=44) | p-value |
|---|---|---|---|---|
| Age (years) | 81 (10) | 79 (11) | 81 (10) | 0.235[1] |
| Male (%) | 40% (n=30) | 42% (n=44) | 36% (n=16) | 0.795[2] |
| Number of injections | 9.9 (7.0) | 12.4 (9.7) | NA | 0.062[1] |
| Glaucoma (%) | 20% (n=15) | 13% (n=13) | 25% (n=11) | 0.147[2] |
| Single drops (%) | 8% (n=6) | 5% (n=5) | 11% (n=5) | 0.348[2] |
| Multiple drops (%) | 11% (n=8) | 7% (n=7) | 14% (n=6) | 0.380[2] |
| IOP (mm hg) | 16.0 (3.6) | 14.2 (3.1) | 15.1 (3.1) | 0.081[1] |
| RNFL (um) | 87.8 (13.8) | 88.6 (13.2) | 87.5 (13.2) | 0.879[1] |
| RNFL no glaucoma (um) | 91.2 (11.7) | 89.0 (12.5) | 91.3 (9.5) | 0.444[1] |
| RNFL glaucoma (um) | 75.9 (14.4) | 86.0 (18.1) | 76.3 (16.2) | 0.224[1] |
| RNFL (um) single drop | 82.5 (11.7) | 95.2 (13.4) | 79.0 (8.9) | 0.099[1] |
| RNFL, (um) multiple drops | 70.9 (15.8) | 79.5 (20.7) | 74.0 (21.2) | 0.707[1] |

Figure 1

| | Group 1 Paracentesis (n=75) | Group 2 No Paracentesis (n=104) | Group 3 Control (n=44) | p-value |
|---|---|---|---|---|
| Follow up (months) | 27.7 (17.2) | 31.3 (24.8) | 26.2 (14.5) | 0.324[1] |
| Maximum post injection IOP (mm hg) | 19.1 (7.7) | 54.1 (12.0) | NA | <0.0001[1] |
| Change IOP with injection (mm hg) | 4.5 (7.9) | 39.9 (12.6) | NA | <0.0001[1] |
| Final IOP (mm hg) | 14.5 (3.9) | 14.0 (3.1) | 14.9 (3.2) | 0.543[1] |
| Change RNFLT, all eyes (um) | -1.3 (4.2) | -5.1 (6.0) | -0.9 (3.7) | <0.0001[1] |
| Change RNFLT, no glaucoma (um) | -1.0 (4.3) | -5.1 (6.0) | -0.3 (3.3) | <0.0001[1] |
| Change RNFLT, glaucoma (um) | -2.6 (5.1) | -5.0 (6.5) | -2.6 (5.1) | 0.392[1] |
| Change RNFLT single drops (um) | -1.5 (3.7) | 0.8 (3.0) | -4.6 (3.2) | 0.070[1] |
| Change RNFLT multiple drops (um) | -3.0 (4.6) | -9.6 (4.9) | -1.0 (6.0) | 0.017[1] |

Figure 2

| | Group 1<br>Paracentesis<br>(n=75) | Group 2<br>No Paracentesis<br>(n=104) | Group 3<br>Control<br>(n=44) | p-value |
|---|---|---|---|---|
| Rate change RNFLT, all eyes (um) | -1.10 (5.71) | -3.30 (5.50) | -0.38 (2.54) | 0.0024[1] |
| Rate change RNFLT, no glaucoma (um) | -0.88 (5.92) | -3.54 (5.77) | -0.02 (2.08) | 0.0014[1] |
| Rate change RNFLT, glaucoma (um) | -1.99 (4.87) | -1.65 (2.74) | -1.45 (3.47) | 0.938[1] |
| Rate change RNFLT single drops (um) | -0.46 (2.10) | 0.40 (1.32) | -2.22 (1.44) | 0.078[1] |
| Rate change RNFLT multiple drops (um) | -1.39 (3.71) | -3.39 (2.69) | -0.80 (4.62) | 0.465[1] |

Figure 3

|  | r-value | p-value |
|---|---|---|
| Immediate post injection change IOP (chgIOP) | -0.175 | 0.121 |
| Maximum post injection IOP (mm hg) | -0.109 | 0.382 |

Figure 4

USE OF MEDICATIONS WITH NEUROPROTECTIVE PROPERTIES TO PREVENT OR REDUCE THE RISK OF ISCHEMIA-REPERFUSION INJURY IN A SUBJECT

CROSS-REFERENCE TO RELATED APPLICATIONS

This application claims priority under 35 U.S.C. § 119(e) to U.S. provisional application No. 62/239,639, filed Oct. 9, 2015, the disclosures of which are incorporated herein by reference in their entirety

BACKGROUND OF THE INVENTION

The eye, like other parts of the central nervous system, has limited regeneration capability. Thus, many ocular diseases and injuries such as retinal photic injury, retinal ischemia-reperfusion induced eye injury, chronic intermittent hypoxia related eye injury, age-related macular degeneration (AMD), and free-radical-mediated diseases are difficult to treat. AMD affects as many as 15 million Americans, with 200,000 new cases each year. Of these, approximately 10-15% further develop exudative disease. Intravitreal anti-VEGF injection (IVAV) has revolutionized the treatment of exudative AMD. While AMD was the first, and is still the most common, indication for intravitreal anti-VEGF injections, additional approved indications include central and branch retinal vein occlusion-related macular edema as well diabetic macular edema. These agents may also be used to diminish the effects of proliferative diabetic retinopathy, vitreous hemorrhage, neovascular glaucoma, retinopathy of prematurity, choroidal neovascularization and many other retinovascular diseases. However, IVAV treatment exposes subjects to risk for optic nerve injury and retinal nerve fiber layer (RNFL) loss caused by several mechanisms including decreased neuroprotection (Chauhan et al., Invest Ophthalmol Vis Sci. 2002, 43:2969-76; Weinreb and Khaw, Lancet 2004, 363:1711-1720; Michelson et al., Graefes Arch Clin Exp Ophthalmol. 1998, 236:80-5; Bonomi et al., Ophthalmology, 2000, 107:1287-93; Kaur et al., ClinOphthalmol. 2008, 2:879-89; Moore D et al., Clin Ophthalmol, 2008, 2:849-61; Leung et al., Br J Ophthalmol, 2009, 93:964-8; Nishijima et al., Am J Pathol, 2007, 171:53-67) and transient ischemia-reperfusion injury. The latter results cumulatively in multiple brief episodes of tissue hypoxia similar to those which occur as a result of chronic intermittent hypoxia (CIH) another cause of RNFL loss. Further, an IVAV treatment regimen generally consists of multiple IVAV injections leading to an increase in cumulative risk for RNFL thinning or loss, as well as other risks such as endophthalmitis, intraocular inflammation, hemorrhage, retinal tear or detachment, retinal vascular occlusion, blindness (Falavarjani et al., Eye, 2013, 27:787-94) and an increase in financial cost. Therefore, there is a need in the art for methods of protecting subjects undergoing VEGF treatments such as IVAV from secondary injury, as well as methods for reducing the total number of IVAV injections required for an effective IVAV treatment regimen. The current invention satisfies this need.

SUMMARY OF THE INVENTION

In one embodiment, the invention relates to a method of protecting against ischemia-reperfusion injury in a subject in need thereof, comprising administering a neuroprotective compound to the subject, wherein the subject is selected from the group consisting of a non-glaucomatous subject and a glaucomatous subject not using a neuroprotective compound.

In one embodiment, a subject will experience or has been diagnosed with one or more of a medical condition or a procedure associated with risk of ischemia-reperfusion injury or chronic intermittent hypoxia. In one embodiment, the condition or procedure is selected from the group consisting of retinal ischemia-induced eye injury, age-related macular degeneration, sleep apnea, diabetes, transient ischemic attack, cardiovascular surgery, and cardiac arrest.

In one embodiment, the neuroprotective compound is capable of crossing the blood-brain barrier and the blood-retina barrier. In one embodiment, the compound is administered to the subject by way of an administration route selected from the group consisting of topical, oral and intravenous. In one embodiment, the compound is a therapeutic compound. In one embodiment, the compound is tafluprost.

In one embodiment, the neuroprotective compound is administered to the subject daily for at least three months.

In one embodiment, a subject is further in need of or has been administered an anti-VEGF treatment. In one embodiment, the compound is administered to the subject by way of one or more treatment regimen selected from the group consisting of at least once prior to anti-VEGF treatment and at least once following anti-VEGF treatment.

In one embodiment, a subject will experience or has experienced a procedure associated with risk of ischemia-reperfusion injury. In one embodiment, the subject will experience or has experienced IVAV. In one embodiment, a compound is administered to the subject by way of one or more administration route selected from the group consisting of topical, oral, intravenous, periocular injection and an intraocular implant drug delivery device. In one embodiment, the compound is administered to the subject daily for the duration and for at least three months following an IVAV treatment regimen. In one embodiment, the method of the invention allows that one or more of the time interval between injections is increased and the number of injections is decreased relative to the average time interval and number of injections received respectively by control individuals.

In one embodiment, the invention relates to a method of treating or protecting a subject from RNFL thinning or loss and ischemia-reperfusion injury associated with IVAV treatment, the method comprising performing intraoperative paracentesis on the subject, when the subject has not received a neuroprotective compound prior to receiving an IVAV injection. In one embodiment, the method further comprises administering a neuroprotective compound to the subject at least once following an IVAV injection. In one embodiment, the compound is administered to the subject by way of one or more administration route selected from the group consisting of topical, oral, intravenous, periocular injection and an intraocular implant drug delivery device. In one embodiment, the compound is administered to the subject daily for the duration of an IVAV treatment regimen. In one embodiment, the compound is tafluprost.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1 depicts baseline characteristics of eyes prior to IVAV treatment. Continuous data are presented as mean (standard deviation). Superscript[1] indicates use of ANOVA; superscript[2] indicates use of Chi-square test.

FIG. 2 depicts post-injection data from follow-up examination, an average of 29 months post-injection. Continuous data are presented as mean (standard deviation). Superscript[1] indicates use of ANOVA.

FIG. 3 depicts the rate change in RNFL thinning. Continuous data are presented as mean (standard deviation). Superscript[1] indicates use of ANOVA.

FIG. 4 depicts data showing a correlation between immediate post injection IOP and change in RNFL thinning or loss.

DETAILED DESCRIPTION

The present invention relates to a method of preventing or reducing the risk of ischemia-reperfusion injury in an individual receiving or about to receive an anti-VEGF treatment. In one embodiment, the present invention provides a safer and more effective way to treat ophthalmic disease and to perform ophthalmic surgeries. In one embodiment, the invention relates to a method of prophylaxis and treatment of optic nerve injury and RNFL thinning or loss in a subject. In one embodiment, the invention relates to a method for increasing the interval between IVAV injections during an IVAV treatment regimen. In one embodiment, the invention relates to an IVAV treatment regimen having a reduced number of IVAV injections.

In one embodiment, the invention relates to a method for preventing or reducing optic nerve injury and RNFL thinning or loss in a subject associated with one or more of a degenerative eye condition, an ophthalmic disease and an ophthalmic procedure by administering to the subject a neuroprotective measure or a therapeutically effective amount of a neuroprotective compound. Ophthalmic diseases and degenerative eye conditions that may be treated using the method of the invention include, but are not limited to macular degeneration, including age-related macular degeneration (AMD) and exudative or wet AMD, macular edema secondary to retinal vascular disease including diabetic retinopathy and retinal vein occlusions and intraocular inflammation; various forms of ocular neovascularization including corneal neovascularization, rubeosis, iris neovascularization, neovascular glaucoma, proliferative retinopathy, radiation retinopathy, retinopathy of prematurity, retinal angiomatous proliferans, Coats' disease, Eales' disease, and choroidal neovascularization secondary to numerous causes including uveitis, parafoveal telangectasis, angoid streaks, choroidal rupture, myopia. In one embodiment, the method of the invention may modulate ocular wound healing including following ocular surgery such as trabeculectomy.

In one embodiment, the method of the invention involves administering a neuroprotective compound to a subject in need of or having undergone an anti-VEGF treatment. In one embodiment, the invention relates to a method for reducing the optic nerve injury and RNFL thinning or loss associated with IVAV treatment in a subject, by administering to the subject a neuroprotective measure or a therapeutically effective amount of a neuroprotective compound. In one embodiment, a neuroprotective compound is pharmaceutical used for treatment of glaucoma.

In one embodiment, the method of the invention relates to performing intraoperative paracentesis during IVAV as a neuroprotective measure.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the clinical procedures are those well-known and commonly employed in the art.

As used herein, the articles "a" and "an" refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

As used herein, "autologous" refers to a biological material derived from the same individual into whom the material will later be re-introduced.

As used herein, "allogenic" refers to a biological material derived from a genetically different individual of the same species as the individual into whom the material will be introduced.

A disease or disorder is "alleviated" if the severity of a symptom of the disease or disorder, the frequency with which such a symptom is experienced by a subject, or both, is reduced.

As used herein, a "disease" is a state of health of a subject wherein the subject cannot maintain homeostasis, and wherein if the disease is not ameliorated then the subject's health continues to deteriorate.

As used herein, a "disorder" in a subject is a state of health in which the subjecl is able to maintain homeostasis, but in which the subject's state of health is less favorable than it would be in the absence of the disorder. Left untreated, a disorder does not necessarily cause a further decrease in the subject's state of health.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the terms "effective amount," "pharmaceutically effective amount" and "therapeutically effective amount" refer to a nontoxic but sufficient amount of an agent to provide the desired biological result. That result can be reduction and/or alleviation of the frequency and/or severity of signs, symptoms, or causes of a disease, or any other desired alteration of a biological system. An appropriate therapeutic amount in any individual case may be determined by one of ordinary skill in the art using routine experimentation.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, the term "pharmaceutically acceptable" refers to a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

As used herein, the term "pharmaceutical composition" refers to a mixture of at least one compound of the invention with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the subject such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the subject.

The term "therapeutic" as used herein means a treatment and/or prophylaxis. A therapeutic effect is obtained by suppression, diminution, remission, or eradication of at least one sign or symptom of a disease or disorder state.

To "treat" a disease as the term is used herein, means to reduce the frequency or severity of at least one sign or symptom of a disease or disorder experienced by a subject.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

IVAV, the standard of care associated with multiple ocular diseases, causes an immediate, transient elevation of intraocular pressure (IOP) which temporarily compromises intraocular circulation. The resultant transient ischemia-reperfusion episodes result in ischemic tissue injury similar to that which occurs in sleep apnea, a condition characterized by chronic intermittent hypoxia. The current invention is based on the discovery that VEGF suppression, intended to modulate detrimental angiogenic and vasopermiability effects, also chronically compromises VEGF's physiologic neuroprotective function rendering eyes more susceptible to ischemia-reperfusion injury.

The present invention is based upon the surprising discovery that neuroprotective measures can be used prophylactically and therapeutically in prevention of RNFL thinning or loss and/or ocular ischemia-reperfusion injury associated with intravitreal anti-VEGF treatment. Specifically, both intraoperative paracentesis and administration of neuroprotective anti-glaucoma medications were found to reduce the RNFL thinning or loss when administered to patients receiving IVAV.

In one embodiment, the invention relates to the use of neuroprotective compounds prophylactically and therapeutically in prevention of ischemia-reperfusion injury in a subject undergoing or in need of an anti-VEGF treatment regimen. In one embodiment, the invention relates to the use of neuroprotective compounds prophylactically and therapeutically in prevention of tissue injury due to chronic intermittent hypoxia.

In one embodiment, a neuroprotective measure comprises providing a treatment regimen of a neuroprotective compound to a subject at risk of one or more of RNFL thinning or loss and/or ischemia-reperfusion injury. In one embodiment, a neuroprotective compound is an anti-glaucoma medication. In one embodiment, a neuroprotective measure comprises performing paracentesis. In one embodiment, a combination of paracentesis and a neuroprotective compound is administered to a subject at risk of one or more of RNFL thinning or loss and/or ocular ischemia-reperfusion injury.

Use

A risk of ischemia-reperfusion injury is often associated with vascular and cardiac surgery, but can also be a concern in transplantation surgery or a complication of disease such as diabetes. A similar intermittent tissue injury due to intermittent ischemia may also occur in persons with chronic intermittent hypoxemia due to sleep apnea. The current invention identifies individuals undergoing an anti-VEGF treatment as having an increased risk of complications arising from intermittent tissue ischemia due to ischemia-reperfusion injury, however any individual at risk of intermittent tissue ischemia due to ischemia-reperfusion injury or CIH can benefit from the method of the invention.

Neuroprotective compounds, including but not limited to anti-glaucoma medications, provide a protective measure to reduce the risk of complications arising from ischemic tissue injury. Therefore, in one embodiment, the method of the invention relates to administering a neuroprotective compound to a subject at risk of ischemia-reperfusion injury or CIH. In one embodiment, the subject is about to receive or receiving an anti-VEGF medication. In one embodiment, the method relates to administering a neuroprotective compound to a subject receiving an anti-VEGF medication prior to, concurrent with, or following a procedure or condition associated with risk of ischemia-reperfusion injury or chronic intermittent hypoxia.

In one embodiment, a procedure associated with risk of ischemia-reperfusion injury is an injection. In one embodiment, an injection is an intravitreal injection. In one embodiment, a procedure associated with risk of ischemia-reperfusion injury is a surgical procedure. Non-limiting examples of surgical procedures that are associated with risk of ischemia-reperfusion injury include cardiovascular surgery, liver transplantation surgery, vitrectomy, free autologous tissue transfer, flap surgery, and vascular surgery.

In one embodiment, a procedure associated with risk of ischemia-reperfusion injury and/or CIH is continuous positive airway pressure (CPAP), in an individual having sleep apnea.

In one embodiment, a procedure associated with risk of ischemia-reperfusion injury is a non-medical procedure. In one embodiment, a non-medical procedure associated with risk of ischemia-reperfusion injury is sleep, in a subject having sleep apnea. In one embodiment, a non-medical procedure associated with risk of ischemia-reperfusion injury may include routine or daily activities such as walking, in a subject having diabetes.

In one embodiment, the neuroprotective compound of the invention is provided to a subject receiving or about to receive an anti-VEGF medication. Such a subject may be diagnosed with any disease for which an anti-VEGF medication is indicated. In one embodiment, a subject is diagnosed as having cancer.

In one embodiment, a subject receiving or about to receive an anti-VEGF medication is a subject having an ophthalmic disease or degenerative eye condition. In one embodiment, an ophthalmic diseases or degenerative eye condition is one of macular degeneration, including age-related macular degeneration (AMD) and exudative or wet AMD, macular edema secondary to retinal vascular disease including diabetic retinopathy and retinal vein occlusions and intraocular inflammation; various forms of ocular neovascularization including corneal neovascularization, rubeosis, iris neovascularization, neovascular glaucoma, proliferative retinopathy, radiation retinopathy, retinopathy of prematurity, retinal angiomatous proliferans, Coats' disease, Eales' disease, and choroidal neovascularization secondary to numerous causes including uveitis, parafoveal telangectasis, angoid streaks, choroidal rupture and myopia.

In one embodiment, a subject receiving or about to receive an anti-VEGF medication is at risk of ischemia-reperfusion injury. In one embodiment, a subject receiving or about to receive an anti-VEGF medication is at risk of an ischemia-reperfusion injury associated pathology. In one embodiment, a subject receiving or about to receive an anti-VEGF medication is at risk of RNFL thinning or loss due to ischemia-reperfusion injury.

In one embodiment, a subject receiving or about to receive an anti-VEGF medication at risk of RNFL thinning or loss due to ischemia-reperfusion injury or chronic intermittent hypoxia is a subject not having been diagnosed with glaucoma or not taking a neuroprotective anti-glaucoma medication at the time an anti-VEGF agent or treatment is prescribed or scheduled.

In one embodiment, a neuroprotective measure is administered to a subject about to receive or having received a treatment comprising an anti-VEGF agent. Anti-VEGF agents include, but are not limited to, Bevacizumab (e.g., Avastin®, Genentech/Roche, Inc., South San Francisco, Calif.), Ranibizumab (e.g., Lucentis®, Genentech/Roche, Inc., South San Francisco, Calif.), Pegaptanib (e.g., Macugen®, Eyetech, Inc., Cedar Knolls, N.J.), aflibercept (e.g., Eylea®, Regeneron Pharmaceuticals, Inc., Tarrytown, N.Y.), brolucizumab (Alcon), Conbercept (Lumitin, Chengdu Kang Hong Biotech, approved in China), NT-503 (Neurotech), dexamethasone, an intravitreal implant (e.g., Ozurdex®, Allergan, Inc., Irvine, Calif.), Anecortave acetate, VEGF-trap, Lapatinib (Tykerb), Sorafenib (Nexavar), Sunitinib (Sutent), Axitinib, and Pazopanib, Squalamine lactate, Combretastatin A4 Prodrug, AdPEDF, SiRNA, Cand5, and TG100801.

In one embodiment, the neuroprotective compound of the invention is provided to a subject at risk of ischemia-reperfusion injury or chronic intermittent hypoxia. Such a subject may be diagnosed with diabetes, sleep apnea, transient ischemic attack or a disease requiring one or more of cardiovascular surgery, liver transplantation surgery, vitrectomy, free autologous tissue transfer, flap surgery, and vascular surgery.

In one embodiment, a subject at risk of ischemia-reperfusion injury or chronic intermittent hypoxia is a subject not having been diagnosed with glaucoma or not taking a neuroprotective anti-glaucoma medication.

In one embodiment, ischemia-reperfusion injury and chronic intermittent hypoxia related injury may occur in any tissue or organ. Organs that are susceptible to ischemia-reperfusion injury and chronic intermittent hypoxia related injury include but are not limited to the eye, heart, liver and brain. Thus, any tissue, organ, or organ system may benefit from protection from ischemia-reperfusion injury and chronic intermittent hypoxia related injury using the method of the invention.

Treatment Regimen

The invention is based on the discovery that patients diagnosed as having glaucoma and taking an anti-glaucoma medication prior and subsequent to IVAV treatment had a reduced level of RNFL thinning or loss as compared to patients not using anti-glaucoma medications. Therefore, one aspect of the invention relates to a method of treating or preventing RNFL thinning or loss in a non-glaucomatous individual in need of IVAV through administering to the individual a treatment regimen of a neuroprotective anti-glaucoma medication. In one embodiment, a neuroprotective compound is administered prior to IVAV treatment, subsequent to IVAV treatment or both. In one embodiment, a treatment regimen comprises administering a neuroprotective compound at least once daily for at least 2, at least 3, at least 4, at least 5 or more days prior to an IVAV procedure. In one embodiment, a treatment regimen comprises administering a neuroprotective compound at least once daily for at least 1 day, at least 7 days, at least 10 days, at least 1 month, at least 2 months, at least 3 months, at least 6 months, at least 1 year or more than 1 year following an individual IVAV procedure. In one embodiment, a treatment regimen comprises administering a neuroprotective compound at least once daily for at least 1 day, at least 7 days, at least 10 days, at least 1 month, at least 2 months, at least 3 months, at least 6 months, at least 1 year or more than 1 year following each individual IVAV injection throughout the duration of an IVAV treatment regimen. In one embodiment, a treatment regimen comprises administering a neuroprotective compound at least once daily for at least 2, at least 3, at least 4, at least 5 or more days prior to an IVAV procedure and for at least 1 day, at least 7 days, at least 10 days, at least 1 month, at least 2 months, at least 3 months, at least 6 months, at least 1 year or more than 1 year following an individual IVAV procedure. In one embodiment, a treatment regimen comprises administering a neuroprotective compound at least once daily for at least 2, at least 3, at least 4, at least 5 or more days prior to an IVAV procedure and for at least 1 day, at least 7 days, at least 10 days, at least 1 month, at least 2 months, at least 3 months, at least 6 months, at least 1 year or more than 1 year following each individual IVAV injection throughout the duration of a IVAV treatment regimen.

Most IVAV treatment regimens include multiple IVAV procedures spaced over several months, a year, or even several years. Therefore, in one embodiment, a treatment regimen includes administering a neuroprotective compound to a non-glaucomatous subject in need of IVAV treatment daily during the whole treatment period for multiple IVAV procedures. Further, the administration of the neuroprotective compound of the invention has a benefit in reducing the duration of IVAV treatment or the number of IVAV procedures necessary for treating an ocular condition.

In one embodiment, a neuroprotective measure is administered to a subject about to experience or having experienced IVAV. In one embodiment, the invention relates to therapeutic use of neuroprotective measure for a subject in need of IVAV both prior to and following the surgical procedure (e.g. a daily eye-drop or medication for use prior to and following the procedure). In one embodiment, the invention relates to therapeutic use of neuroprotective measure for a subject in need of IVAV during the surgical procedure (e.g. paracentesis). In one embodiment, the invention relates to therapeutic use of neuroprotective measure for a subject in need of IVAV during and following the procedure (e.g. a combination of paracentesis and a daily eye-drop or medication for use following the procedure). In one embodiment, administration of the neuroprotective compound of the invention has a benefit in reducing one or more of the duration of IVAV treatment and the number of IVAV procedures necessary for treating an ocular condition.

In one embodiment, a neuroprotective compound is administered for at least 1, 2, 3, 4, 5, 6, 7, 8, 9, 10, or more than 10 days prior to administration of an anti-VEGF agent. In one embodiment, a neuroprotective compound is administered daily for at least 1 day, at least 7 days, at least 10 days, at least 1 month, at least 2 months, at least 3 months, at least 6 months, at least 1 year or more than 1 year following administration of an anti-VEGF agent. In one embodiment, a neuroprotective compound is administered chronically.

In one embodiment, a neuroprotective compound is administered to a subject taking an anti-VEGF agent for at least 1, 2, 3, 4, 5, 6, 7, 8, 9, 10, or more than 10 days prior to a surgical procedure. In one embodiment, a neuroprotective compound is administered to a subject taking an anti-VEGF agent daily for at least 1 day, at least 7 days, at least 10 days, at least 1 month, at least 2 months, at least 3 months, at least 6 months, at least 1 year or more than 1 year following a surgical procedure. In one embodiment, a neuroprotective compound is administered chronically.

In one embodiment, a neuroprotective measure is used in combination with a neuroprotective compound. In one embodiment, intraoperative paracentesis is used in combination with a treatment regimen comprising a neuroprotective compound. Such a combination may be useful in protecting a subject from RNFL thinning or loss when the subject has not been administered a neuroprotective compound prior to receiving IVAV. In one embodiment, a subject who has not been administered a neuroprotective compound is a subject who has not been provided with or who has not taken a neuroprotective compound at least once daily for at least 2, at least 3, at least 4, at least 5 or more days prior to an IVAV procedure.

Treat and Extend

The treat-and-extend strategy (T&E) generally begins with monthly loading injection(s)—generally 1-3—after which the patient returns in 4 weeks and is evaluated for signs of disease activity. The patient receives an injection and if the disease is active, returns in 4 weeks for another; if no evidence of disease activity is seen, the patient returns in 5 or 6 weeks. The patient receives an injection at each visit with the results of the examination determining the interval to the next visit. If inactive, the interval is extended by 1 or 2 weeks; if active, the interval is decreased by 2 weeks and then kept constant. Generally, once the optimal treatment interval is determined for a given eye, it usually remains constant.

In one embodiment, the method of the invention is used with a T&E strategy to one or more of reduce the total number of IVAV injections that an individual receives and increase the interval between IVAV injections. In one embodiment, the method reduces the number of initial monthly loading IVAV injections. In one embodiment, the method allows for a higher percentage of patients to be extended to the maximum recommended interval between IVAV injections (generally 10-12 weeks).

Compounds

Neuroprotective compounds that may be administered according to the invention include, but are not limited to, acetazolamide, alpha agonists, betaxolol, bimatoprost 0.01% ophthalmic solution, bimatoprost 0.03% ophthalmic solution, brimonidine, brinzolaminde, a combination of brimonidine plus brinzolamide, Ca2+ channel blockers, carbonic anhydride inhibitors, chondroitin sulfate proteoglycan, dorzolamide, ginkgo biloba extract, latanoprost, L-glutamate, memantine, neurotrophins, nipradilol, Nitric Oxide Synthase inhibitors, NMDA antagonists, phenylephrine, prostaglandin analogues, tafluprost, timolol, timolol XE, a combination of timolol plus brimonidine, travoprost 0.004% eye drop, travoprost 0.004% eye drop-Travatan Z and unoprostone isopropyl ophthalmic solution, nalmefene, minocycline, recombinant human basic fibroblast growth factor (bFGF), citicoline, green tea extract and epoetin alfa. In one embodiment, a neuroprotective compound is an anti-glaucoma medication.

In one embodiment, a composition comprising a neuroprotective compound is preservative free. In one embodiment, a preservative free neuroprotective compound is tafluprost.

In another embodiment of the invention, a therapeutically effective amount of a neuroprotective compound is used in combination therapy with a broad range of presently available ocular therapeutics. Hence, a neuroprotective compound can be coadministered with at least one other therapeutically active agent in the same delivery vehicle/carrier either topically, orally, or intravenously. Alternatively, the combination therapy can be coadministered using separate routes and dosage forms, (e.g., neuroprotective eye drop and oral antibiotic). Within the scope of the invention, a neuroprotective measure or compound is efficaciously combined with at least one of an antibiotic (e.g., beta-lactam type, fluoroquinolones, peptide antibiotics, broad-spectrum penicillins, fortified antibiotic mixtures), an antibacterial, a free-radical scavenging antioxidant, an antiviral, a corticosteroid, a non-steroidal anti-inflammatory, a cycloplegic, a cholinergic, an aqueous or saline irrigating solution, a miotic, a collagenase inhibitor, a carbonic anhydrase inhibitor, a glycoprotein, a growth factor, silver nitrate, and an ocular tissue adhesive/corneal mortar (for acutely inflamed perforated corneas).

In one embodiment, a neuroprotective measure or compound can be coadministered with a therapeutically effective amount of an antibiotic exemplified by ciprofloxacin, ofloxacin, norfloxacin, cefazolin, tobramycin, gentamycin, an aminoglycoside, a penicillin, a semisynthetic penicillin, amoxicillin, ampicillin, carbenicillin, ticarcillin, mezlocillin, a cephalosporin, vancomycin, chloramphenicol, erythromycin, clindamycin, rifampin, bacitracin, polymyxin, spectinomycin, a sulfonamide; and trimethoprim; a free-radical scavenging antioxidant exemplified by super oxide dismutase, a carotenoid (such as astaxanthin, canthazanthin, β-carotene, zeaxanthin, lutein and α-tocopherol), ascorbic acid, glutathione, selenous acid or sodium selenate, and certain aminosteroids (e.g., as disclosed in U.S. Pat. No. 5,209,926); an antiviral exemplified by acyclovir, ganciclovir, idoxuridine, vidarabine, trifluridine, bromovinyldeoxyuridine, azidothymidine, amantadine, rimantadine; a corticosteroid exemplified by dexamethasone, prednisolone, prednisone, fluorometholone, betamethasone, hydrocortisone; an non-steroidal antiinflammatory agent exemplified by ketorolac, indomethacin, flurbiprofen, ketoprofen, loxoprofen, and diclofenac; a cycloplegic exemplified by atropine; a moitic exemplified by physostigmine, pilocarpine, and carbachol; a collagenase inhibitor exemplified by acetyl cysteine; a glycoprotein such as fibronectin and vitronectin, as well as analogs or fragments thereof, an ocular tissue adhesive as exemplified by isobutyl cyanoacrylate; a corneal mortar exemplified by fibronectin/growth factor (e.g., EGF) composition, optionally with a protein crosslinking agent (e.g., aldehydes and di-imidate esters); and various admixtures of the above materials.

The precise neuroprotective measure or prophylactic or therapeutic dosage of a neuroprotective compound to be employed depends upon several factors, including the age and physical condition of the subject, the nature and the severity of the ocular condition being treated, and the route of dosage administration. The assessment of these factors as well as the determination of the precise dosage is well within the skill of the treating ophthalmologist. In one embodiment, a neuroprotective compound is administered in an amount or at a dose that does not result in substantial toxicity to the eye. As used herein, a lack of substantial toxicity encompasses both the absence of any manifestations of toxicity, as well as manifestations of toxicity that one skilled in the art would consider not sufficiently detrimental to decrease or cease treatment.

Formulations and Administration

Administration of the neuroprotective measures or compounds of the present invention to a subject, preferably a mammal, more preferably a human, may be carried out using known procedures, at dosages and for periods of time effective to prevent or treat one or more of ischemic tissue injury due to ischemia-reperfusion injury or CIH, and RNFL thinning or loss in the subject. An effective amount of the therapeutic compound necessary to achieve a therapeutic effect may vary according to factors such as the state of the disease or disorder in the subject; the age, sex, and weight of the subject; and the ability of the therapeutic compound to cross the blood-brain barrier and the blood-retina barrier The regimen of administration may affect what constitutes an effective amount. The neuroprotective measure or compounds may be administered to the subject one or more of prior to, during and after IVAV treatment or the administration of an anti-VEGF agent. Further, the dosages of the neuroprotective compounds may be proportionally increased or decreased as indicated by the exigencies of the therapeutic or prophylactic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular subject, composition, and mode of administration, without being toxic to the subject.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the subject being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

Compounds of the invention for administration may be in the range of from about 1 μg to about 10,000 mg, about 20 μg to about 9,500 mg, about 40 μg to about 9,000 mg, about 75 μg to about 8,500 mg, about 150 μg to about 7,500 mg, about 200 μg to about 7,000 mg, about 3050 μg to about 6,000 mg, about 500 μg to about 5,000 mg, about 750 μg to about 4,000 mg, about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., an apicomplexan parasite anti-infective) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments therebetween.

Eye drops and intravitreal or periocular (Sub-Tenon or subconjunctival) injections are the conventional dosage forms that account for greater than ninety percent of the currently available ophthalmic formulations. To improve bioavailability and reduce the complications associated with repeated injections, the present invention contemplates sustained delivery of neuroprotective compounds alone or in combination with other medications. The sustained delivery in the present invention can be achieved through a number of different delivery systems, including but not limited to polymeric gels, colloidal systems including liposomes and nanoparticles, cyclodextrins, collagen shields, diffusion chambers, flexible carrier strips, and intravitreal implants.

In the present invention, ocular and intraocular drug delivery systems deliver these neuroprotective compounds to the back of the eye. These drug delivery systems include: using the sclera itself as a drug delivery reservoir, "prodrug" formulations that pass through the tissue, tiny biodegradable pellets that release the combinations over time, intravitreal implants, intravitreal silicone inserts, intravitreal and transscleral poly(lactic-co-glycolic acid) microspheres, calcium-alginate inserts, encapsulated cells, transscleral iontophoresis, nanoparticles (e.g., calcium phosphate), and genetically modified viruses that can deliver therapeutic proteins into therapy.

Neuroprotective compounds of the present invention can be in the form of solutions. Solutions can be administered topically by applying them to the cul-de-sac of the eye from a dropper controlled bottle or dispenser. A typical dose regimen for an adult human may range from about 2 to about 8 drops per day, applied at bed-time or throughout the day. Dosages for adult humans may, however, be higher, in which case the drops are administered by "bunching", e.g., 5 doses administered over a 5 minute period, repeated about 4 times daily. A topical solution in accordance with one embodiment of the invention comprises a therapeutic dose of a neuroprotective compound in an artificial tear formulation. Such artificial tear formulations are used for restoring the normal barrier function of damaged corneal epithelium following surgery. Typically, artificial tear compositions contain ionic components found in normal human tear film, as well as various combinations of one or more of tonicity agents (e.g., soluble salts, such as Na, Ca, K, and Mg chlorides, and dextrose and sorbitol), buffers (e.g., alkali metal phosphate buffers), viscosity/lubricating agents (e.g., alkyl and hydroxyalkyl celluloses, dextrans, polyacrylamides), non-ionic surfactants, sequestering agents (e.g., disodium edetate, citric acid, and sodium citrate), and preservatives (e.g., benzalkonium chloride, and thimerosal). In one embodiment, artificial tear compositions are preservative free. The quantities and relative proportions of each of these components incorporated into an artificial tear composition are readily determinable by the skilled formulation chemist. The ionic species bicarbonate is used in artificial tear compositions, e.g., U.S. Pat. No. 5,403,598 and Ubels, J L, et al, Arch. Ophthalmol. 1995, 113: 371-8.

Alternatively, neuroprotective compounds of the present invention can be in the form of ophthalmic ointments. Ophthalmic ointments have the benefit of providing prolonged drug contact time with the eye surface. Ophthalmic ointments will generally include a base comprised of, for example, white petrolatum and mineral oil, often with anhydrous lanolin, polyethylene-mineral oil gel, and other substances recognized by the formulation chemist as being non-irritating to the eye, which permit diffusion of the drug into the ocular fluid, and which retain activity of the medicament for a reasonable period of time under storage conditions.

Prophylactic and therapeutic amounts of a neuroprotective compound can be administered orally. For these oral dosage forms, a neuroprotective compound may be formulated with a pharmaceutically acceptable solid or liquid carrier. Solid form preparations include powders, tablets, pills, capsules, cachets, and dispersible granules. The concentration or effective amount of the neuroprotective compound to be administered per dosage is widely dependent on the actual compound. However, a total oral daily dosage normally ranges from about 50 mg to 30 g, and more preferably from about 250 mg to 25 g. A solid carrier can be one or more substances which may also function as a diluent, a flavoring agent, a solubilizer, a lubricant, a suspending agent, a binder, a preservative, a tablet disintegrating aid, or an encapsulating material. Suitable carriers include magnesium carbonate, magnesium stearate, talc, sugar, lactose, pectin, dextrin, starch gelatin, tragacanth, methylcellulose, sodium carboxymethylcellulose, microcrystalline cellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills cachets, and lozenges can be used as solid dosage forms suitable for oral administration.

A neuroprotective compound may also be administered surgically as an ocular implant. As one example, a reservoir container having a diffusible wall of polyvinyl alcohol or polyvinyl acetate and containing milligram quantities of a neuroprotective compound may be implanted in the sclera. As another example, a neuroprotective compound in milligram quantities may be incorporated into a polymeric matrix having dimensions of about 2 mm by 4 mm, and made of a polymer such as polycaprolactone, poly(glycolic) acid, poly (lactic) acid, or a polyanhydride, or a lipid such as sebacic acid, and may be implanted on the sclera or in the eye. This is usually accomplished with the subject receiving either a topical or local anesthetic and using a small (3-4 mm incision) made behind the cornea. The matrix, containing a neuroprotective compound, is then inserted through the incision and sutured to the sclera using 9-0 nylon.

A neuroprotective compound may also be contained within an inert matrix for either topical application or injection into the eye. As one example of an inert matrix, liposomes may be prepared from dipalmitoyl phosphatidylcholine (DPPC), preferably prepared from egg phosphatidylcholine (PC) since this lipid has a low heat transition. Liposomes are made using standard procedures as known to one skilled in the art. A neuroprotective compound, in amounts ranging from nanogram to microgram quantities, is added to a solution of egg PC, and the lipophilic drug binds to the liposome.

A time-release drug delivery system may be implanted intraocularly to result in sustained release of the active agent over a period of time. The implantable formation may be in the form of a capsule of a polymer (e.g., polycaprolactone, poly(glycolic) acid, poly(lactic) acid, polyanhydride) or lipids that may be formulation as microspheres. As an illustrative example, a neuroprotective compound may be mixed with polyvinyl alcohol (PVA), the mixture then dried and coated with ethylene vinyl acetate, then cooled again with PVA. The neuroprotective compound bound with liposomes may be applied topically, either in the form of drops or as an aqueous based cream, or may be injected intraocularly. In a formulation for topical application, the drug is slowly released overtime as the liposome capsule degrades due to wear and tear from the eye surface. In a formulation for intraocular injection, the liposome capsule degrades due to cellular digestion. Both of these formulations provide advantages of a slow release drug delivery system, allowing the subject a constant exposure to the drug over time.

In a time-release formulation, the microsphere, capsule, liposome, etc. may contain a concentration of a neuroprotective compound that could be toxic if administered as a bolus dose. The time-release administration, however, is formulated so that the concentration released at any period of time does not exceed a toxic amount. This is accomplished, for example, through various formulations of the vehicle (coated or uncoated microsphere, coated or uncoated capsule, lipid or polymer components, unilamellar or multilamellar structure, and combinations of the above, etc.). Other variables may include the subject's pharmacokinetic-pharmacodynamic parameters (e.g., body mass, gender, plasma clearance rate, hepatic function, etc.). The formation and loading of microspheres, microcapsules, liposomes, etc. and their ocular implantation are standard techniques known by one skilled in the art, for example, the use a ganciclovir sustained-release implant to treat cytomegalovirus retinitis, disclosed in Vitreoretinal Surgical Techniques, Peyman et al., Eds. (Martin Dunitz. London 2001, chapter 45); Handbook of Pharmaceutical Controlled Release Technology, Wise, Ed. (Marcel Dekker, New York 2000), the relevant sections of which are incorporated by reference herein in their entirety.

A further aspect of the invention is intraoperative paracentesis. For administration of intraoperative paracentesis, anesthesia may be administered via methods known to those of skill in the art including, but not limited to, topical administration of proparacaine or tetracaine drops, 2% lidocaine gel or subconjunctival injection of 2% lidocaine solution. In general, intravitreal injections are administered under controlled aseptic conditions, using mask, sterile gloves, a sterile drape, and a sterile lid speculum. Prior to injection the periocular area is cleaned. Solutions for use in cleaning the periocular area are known to those of skill in the art and may include a povidone-iodine preparation. Intraoperative paracentesis (PARA) may be performed immediately following an intravitreal injection, such as IVAV. PARA may be performed by methods known to those of skill in the art including, for example, using a 30 g needle on a tuberculin syringe from which the plunger had been removed. Following PARA, irrigation of the eyes may be performed with an appropriate solution. In one embodiment, a solution appropriate for use is a balanced salt solution.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Effect of Intravitreal Anti-VEGF Injection Performed with and without Paracentesis on Retinal Nerve Fiber Layer Thickness In a previous study, a trend towards RNFL thinning or loss in eyes that received IVAV without adjunctive paracentesis (PARA) was observed (Hale et al., The Retina Society Annual Meeting, 2010). However, this study was limited by retrospective design, small sample size, small number of injections and short follow-up period. The purpose of the present study is to investigate the impact of IVAV performed with and without PARA on RNFL thinning or loss.

The materials and methods are now described.

Materials and Methods

Trial Design

This cohort study compared IVAV with and without PARA in two parallel groups with AMD followed for at least 3 months. The study was performed at a single institution in northeastern Pennsylvania.

Study Population

The study population included all Geisinger Medical Center subjects who began treatment with IVAV between January 2008 and May 2014. The scheduling staff, which was blinded to the study treatments, assigned eight hundred eighty three subjects to one of two retina specialists. One physician performed paracentesis on all subjects, while the other did not perform paracentesis on any subject. Number of potential subjects was smaller in the PARA subgroup because that physician worked fewer days per week at the study location. Each retina specialist alerted the Clinical Research Coordinator (CRC) about potential study participants at the time of the initial exam. The CRC discussed the study with candidates and those who accepted the invitation to participate and who met inclusion criteria (168 subjects, 196 eyes) were enrolled. Five eyes (3 subjects) with poor quality OCT due to media opacity or poor fixation, 8 eyes (8 subjects) with juxtapapillary neovascularization and 4 eyes (4 subjects) with fewer than 3 months follow up were excluded, resulting in 179 eyes of 153 subjects. The Geisinger Institutional Review Board approved the study. Written informed consent was obtained from all participants and the study was conducted in accordance with the Declaration of Helsinki. The study was HIPAA compliant. All testing and treatment was performed in the Geisinger Medical Center Department of Ophthalmology in Danville, Pa., USA.

Assessments

Ophthalmic photographers obtained OCT (Cirrus, Carl Zeiss Meditec, Inc.) prior to each injection and scanned images into the electronic medical record. RNFL thickness was calculated by the autosegmentation algorithm. An ophthalmic nurse obtained intraocular pressure with tonopen before and immediately and 10 minutes after injection. Tonopen was used in lieu of applanation in order to facilitate immediate post-injection IOP measurement. If the 10-minute post injection IOP was greater than 30 mm hg, additional IOP readings were obtained at 10 minute intervals until IOP was 30 mm hg or less.

Outcomes

The primary outcome measures were the mean change in RNFL thinning or loss (chgRNFL thinning or loss) between initial and final measurements and the rate of RNFL thinning or loss change (rate chgRNFLT). Secondary outcomes calculated for each visit were the mean pre to post injection change of IOP (chgIOP) and the maximum post injection IOP (maxIOP) and final IOP. The highest maxIOP and the largest chgIOP recorded for each eye throughout the course of treatment were used to compute mean values. IOP prior to injection at last visit was recorded as final IOP. Adverse events monitored included endophthalmitis, hyphema, lens injury, pre-injection IOP>25.

Intervention

Intravitreal injections were performed using 0.05 ml of one of three anti-VEGF medications (ranibizumab, bevacizumab, aflibercept) at the discretion of the treating physician. Following 3 initial consecutive monthly injections, re-injections were performed according to "treat and extend" protocol based on OCT findings. No attempt was made to standardize injection interval between groups. Anesthesia depended on subject and physician preference, and methods included topical proparacaine or tetracaine drops, 2% lidocaine gel or subconjunctival injection of 2% lidocaine solution. Pre-injection prep varied with physician preference. In PARA eyes eyelids were prepped with 10% betadine swab and additional betadine instilled into the conjunctiva. In non-PARA eyes, no eyelid prep was performed and betadine was applied to the conjunctiva using a 10% betadine swab immediately prior to injection. Masking was not used routinely in either group. Injection was delivered by 30 g needles through the pars plana in either the superotemporal or inferotemporal quadrant according to physician preference. A cotton tipped applicator was placed over the injection site. Paracentesis was performed at the temporal limbus immediately after injection using a 30 g needle on a tuberculin syringe from which the plunger had been removed. Following injection, all eyes were irrigated with balanced salt solution. Between 2008 and 2013 topical antibiotics were prescribed in both groups, and thereafter no prophylactic antibiotics were used.

Statistical Analysis

Data were summarized using means with standard deviations (continuous data) or percentages (categorical data). Baseline characteristics were compared between the PARA group (group 1), the non-PARA group (group 2), and the control group (group 3) using analysis of variance (ANOVA) or Chi-square test, as appropriate. Post injection outcomes were evaluated by comparing maximum post injection IOP, change in IOP from baseline to post injection, final IOP, change in RNFL thinning or loss and rate of change in RNFL thinning or loss between the treatment groups using ANOVA. Pearson's correlation coefficient was used to measure the extent of correlation between the IOP outcomes, change in RNFL thinning or loss and rate change in RNFL thinning or loss. SAS version 9.3 was used for statistical analysis, all tests were two-sided, and p-values<0.05 were considered significant. Multiple linear regression adjusting for age, gender, number of injections, follow-up time, baseline RNFL thinning or loss, and baseline IOP was used to determine if differences between groups remained after accounting for potential biases.

The results are now described.

Results

One hundred seventy nine eyes of 153 subjects who met the entry criteria were included. Baseline characteristics are presented in FIG. 1. Seventy-five eyes received PARA (group 1) and 104 eyes did not (group 2). An additional 44 untreated fellow eyes served as controls (group 3). Mean age was 81.0 and 79.0 years in groups 1 and 2 respectively. Forty percent of subjects in group 1 and 42% in group 2 were male. Mean number of injections was 9.9 (group 1) and 12.4 (group 2). Glaucoma, defined by presence of EMR diagnosis of glaucoma and either use of topical anti-ocular hypertensive drops or history of filtering procedure, was present in 20% (15 eyes) of group 1, 13% (13 eyes) of group 2 ($p=0.147$) and in 25% (11 eyes) controls. Of these, 11% (8 group 1 eyes) and 7% (7 group 2 eyes) were taking multiple anti-ocular hypertensive drops. At baseline mean IOP was 16.0 mmhg (group 1) and 14.2 mmhg (group 2). Baseline mean RNFL thinning or loss was 87.8 um in group 1 and 88.6 um in group 2. There were no statistically significant differences among baseline parameters.

FIG. 2 presents post injection data. Mean follow-up was 27.7 and 31.3 months in groups 1 and 2 respectively. Mean maxIOP was 19.1 mm hg and 54.1 mm hg in groups 1 and 2 respectively ($p<0.0001$). Mean chgIOP was 4.5 mm hg (range −15 to 24) after paracentesis and 39.9 mm hg (range 13 to 60) in non-paracentesis eyes ($p<0.0001$). Mean chgRNFL thinning or loss was −1.3 um (group 1), −5.1 um (group 2) ($p<0.0001$) and −0.9 um (group 3). Mean pre-injection IOP at final visit (final IOP) were 14.5 and 14.0 in groups 1 and 2 respectively. There was no statistically significant change in pre-injection IOP between initial and final visits in either group. Among eyes without glaucoma, mean chgRNFL thinning or loss was −1.0 um and −5.1 um in groups 1 and 2 respectively ($p<0.0001$) and −0.3 um in controls. Mean chgRNFL thinning or loss was −2.6 um (group 1), −5.0 um (group 2) ($p=0.392$) and −2.6 um (control) in glaucomatous eyes. Among glaucomatous eyes taking multiple drops, chgRNFL thinning or loss was −3.0, −9.6, −1.0 um in groups 1, 2 and controls respectively ($p=0.017$). Neither chgIOP ($r=-0.175$, p-value=0.121), nor maxIOP ($r=-0.109$, p-value=0.382) was significantly correlated with chgRNFLT.

Similar results were found when using multiple linear regression accounting for age, gender, number of injections, follow-up time, baseline RNFL thinning or loss, and baseline IOP. In these models, maxIOP, chgIOP, and chgRNFL all remained significant ($p<0.0001$ for each) and final IOP remained not significant ($p=0.173$). We checked all of the interactions between baseline factors and confirmed that their inclusion in the models do not change the results presented.

FIG. 3 provides rate of RNFL thinning or loss change. Mean rate chgRNFL thinning or loss was −1.1 um/year vs. −3.3 um/year in groups 1 and 2 respectively ($p=0.0024$). Subgroup analysis of eyes without glaucoma revealed mean rate chgRNFL thinning or loss was −0.88 um/year vs −3.54 um/year in groups 1 and 2 respectively ($p=0.0014$). Among all glaucomatous eyes, mean rate chgRNFL thinning or loss of −1.99 um/year, −1.65 um/year and −1.45 um/year in groups 1 and 2 and controls respectively ($p=0.938$) and in those taking multiple drops it was −1.39 um/year vs. −3.39 um/year in groups 1 and 2 ($p=0.465$). Standard deviations were included with means to provide a sense of the underlying distributions. The distribution of change in RNFL and rate of change in RNFL resemble a bell shaped curve. If outliers are defined as +/−4 standard deviations from the mean, there were no outliers for change in RNFL. For rate of change in RNFL, there were 3 outliers. A sensitivity analysis was conducted by removing the outliers and comparing the results to those in FIG. 3. This sensitivity analysis revealed no changes to the results in FIG. 3, suggesting that the outliers are not affecting the results presented.

Two eyes developed a single episode of pre-injection IOP>25 during the course of therapy. Endophthalmitis requiring vitreous tap and intravitreal antibiotic injection developed in 2 group 2 eyes (2 subjects) (0.16% of injections, 1.9% of subjects). Both subjects received prophylactic topical antibiotics after anti-VEGF injection (erythromycin ointment TID, ofloxacin drops QID). No paracentesis eye developed hyphema or iris or lenticular injury.

Studies of the effect of IVAV on RNFL thinning or loss have reached conflicting conclusions. In a prospective study of 49 eyes followed for 12 months, Martinez-de-la Casa et al found intravitreal ranibizumab injections used to treat AMD caused significant RNFL thinning or loss thinning (Martinez-de-la-Casa et al., Invest Ophthalmol Vis Sci. (2012) 53(10):6214-6218). Three smaller retrospective series, two of which used time domain rather than spectral domain OCT, did not detect RNFL thinning or loss (Sobaci et al., Int J Ophthalmol. 2013; 6(2):211-215; Demirel et al., Curr Eye Res. 2015; 40(1):87-92; Horsley et al., Am J Ophthalmol 2010; 150:558-561). The data demonstrates a statistically significant loss of RNFL thinning or loss in non-glaucomatous eyes that received IVAV without paracentesis.

Previous studies have reported intermittent or sustained elevation of baseline IOP in 3-6% of eyes during the course of treatment with IVAV (Adelman et al., J Ocular Pharmacol Ther. 2010; 26(1):105-110; Good et al., Br J Ophthalmol. 2011; 95(8):1111-1114; Tseng et al., J Glaucoma. 2012; 21(4):241-247; Bakri et al., Ophthalmology. 2014; 121: 1102-1108). A significant difference between mean initial and final baseline IOPs was not identified. The mean follow-up is shorter and mean number of injections is smaller than those reported by Tseng (Tseng et al., J Glaucoma. 2012; 21(4):241-247), however, without being bound to a particular theory, it does not appear that sustained elevation of baseline IOP was responsible for the RNFL thinning or loss observed in this study.

Intravitreal injection of 0.05-0.10 ml volume causes transient increased IOP (Falkenstein et al., Retina. 2007; 27(8): 1044-1047; Kim et al., Am J Ophthalmol. 2008; 146(6): 930-934; Sharei et al., Eur J Ophthalmol. 2010; 20(1):174-179; Gismondi et al., J Glaucoma. 2009; 18(9):658-661). Animal studies have demonstrated reduction of blood flow and tissue oxygenation at intraocular pressures greater than 50 mm hg and ocular perfusion pressure lower than 30 mm hg (Shonat et al., Invest Ophthalmol Vis Sci. 1992; 33(11): 3174-3180) as well as retinal ganglion cell damage when IOP of 110 mm hg is sustained for 90 minutes (Leung et al., Br J Ophthalmol. 2009; 93(7):964-968). Maximum change in IOP has been correlated with progressive optic nerve cupping in rats (Chauhan et al., InvestOphthalmol Vis Sci. 2002; 43 (9):2969-2976). In humans, ocular perfusion and ischemia depends in part upon IOP and may be modulated by systemic vascular factors (Deb et al., Indian J Ophthalmol. 2014; 62(9):917-922; Wang et al., Curr Eye Res. 2014; 9:1-9; Yip et al., Invest Ophthalmol Vis Sci. 2011; 52(11): 8186-8192). Mean maxIOP and mean chgIOP for group 2 eyes in this study was higher than what has been reported previously (Kim et al., Am J Ophthalmol. 2008; 146(6):930-934; Sharei et al., Eur J Ophthalmol. 2010; 20(1):174-179; Gismondi et al., J Glaucoma. 2009; 18(9):658-661). Among recognized factors (Falkenstein et al., Retina. 2007; 27(8): 1044-1047; Kim et al., Am J Ophthalmol. 2008; 146(6): 930-934; Sharei et al., Eur J Ophthalmol. 2010; 20(1):174-179; Gismondi et al., J Glaucoma. 2009; 18(9):658-661; Bakri et al., Eye. 2009; 23(1):181-185) routine use of 30 g needles may have contributed. Nonetheless, neither chgIOP nor maxIOP was significantly correlated with chgRNFL thinning or loss.

VEGF-A is required for the maintenance of normal retinal ganglion cells (Nishijima et al., Am J Pathol. 2007; 171(1): 53-67) and inhibition of VEGF's maintenance effect has the potential to cause RNFL injury. RNFL thinning or loss in group 1 eyes treated with anti-VEGF agents and paracentesis did not differ from that observed in fellow eye controls. Although a crossover effect of systemically absorbed anti-VEGF agents in fellow eyes cannot be excluded (Scartozzi et al., Eye 2009, 23:1229; Bakbak et al., J Ocul Pharmacol Ther. 2013, 29:728-32; Bakbak et al., Oman J Ophthalmol. 2016, 9:44-8) and VEGF inhibition may account for the modest RNFL thinning or loss observed in both groups. However, the effect of VEGF inhibition alone does not account for the significant difference in chgRNFLT observed between PARA and non-PARA groups.

Transient tissue ischemia injury may be caused by ischemia-reperfusion and chronic intermittent hypoxia. Ischemia-reperfusion injury has been modeled in skin using intermittent mechanical compression simulating diabetic foot ulcers (Reid R R, et al. J Surg Res. 2004 January; 116:172-80.31) and with vascular occlusion simulating transient ischemic attacks (TIA) (Lee et al., AJNR 2004 25:1342-7). Sleep apnea has been associated with RNFL loss (Ferrandez et al. BMC Ophthalmol. 2016, 16:40; Zhao et al. J Glaucoma 2016; 25:e413-8).). Chronic intermittent hypoxia has been modeled using brief periods of hypoxia simulating sleep apnea in neural (Gozal D, et al. J Neuroscience, 2001, 21: 2442-50; Guo et al., Zhonghua Er Bi Yan Hou Tou Jing Wai Ke Za Zhi. 2016, 51:282-532) and cardiac (Park et al. Appl Physiol. 2007; 102(5):1806-14) tissues.

Without being bound to a particular theory, it is believed that immediate post injection IOP elevation in non-PARA eyes reduces perfusion and causes a transient period of tissue ischemia. As IOP normalizes, reperfusion occurs. Tissue damage occurs as blood supply is re-established after a period of hypoxia or ischemia. VEGF confers neuroprotection (Sun et al., J Clin Invest. 2003; 111(12):1843-1851; Silverman et al., Neuroscience. 1999; 90:1529-1541; Jin et al., PNAS 2000; 97: 10242-10247; Matsuzaki et al., FASEB J. 2001; 15:1218-1220) and has been shown to reduce infarct size (Dzietko et al., Transl. Stroke Res. 2013, 4:189-200; Zhang, et al., J. Clin. Investig. 2000, 106:829-838; Zhang et al., J. Cerebr. Blood Flow Metab. 2002, 22:379-392; Zhang, et al., Mol. Med. Rep. 2012, 6:1315-18) and apoptosis (Zhang, et al., Mol. Med. Rep. 2012, 6:1315-18) and increase neurogenesis after stroke (Yang et al., Neuromol. Med. 2014, 16:376-8843). VEGF also protects retinal ganglia from ischemia-reperfusion injury (Nishijima et al., Am J Pathol. 2007; 171(1):53-67; Hirooka et al., Invest Ophthalmol Vis Sci. 2006; 47(4):1653-1657). VEGF-A blockade exacerbates ganglion cell death due to ocular hypertension (Foxton et al., Am J Pathol 2013; 182(4):1379-90) and increases infarct volume following focal transient cerebral ischemia (Bao et al., Zhongguo Yao Li Xue Bao. 1999, 20:313-8). In this regard, chronic VEGF inhibition intended to modulate detrimental angiogenic and vasopermiability effects may also chronically compromise VEGF's physiologic neuroprotective function and limit the ability of the RNFL to tolerate even brief episodes of transient ischemia-reperfusion associated with IVAV.

Contrary to what was expected, non-PARA eyes with glaucoma did not develop significant RNFL thinning. All were being treated with topical ocular anti-hypertensive agents. The neuroprotective effects of topical ocular anti-hypertensive drops (Shih et al., Expert Rev Ophthalmol. 2012; 7(2): 161-175) may have compensated for the loss of VEGF-derived neuroprotection or acted synergistically with residual VEGF and thereby limited RNFL thinning or loss in these eyes.

Chronic VEGF inhibition due to IVAV, periocular injection, systemic administration or topical administration may also limit the ability of the RNFL to tolerate transient ischemia-reperfusion injury. Further, because VEGF enters the systemic circulation following IVAV and reduce systemic anti-VEGF levels (Hård et al., Acta Paediatr, 2011, 100:1523-7; Avery et al., Ophthalmology, 2006 113:1695; Qian et al., Retina, 2011, 31:161-8) they may render other tissues and organs normally protected by VEGF (Sun Y et al. J Clin Invest. 2003; 111(12):1843-51; Silverman, W F et al. Neuroscience. 1999; 90:1529-41; Jin K L et al. PNAS 2000;

97: 10242-7; Matsuzaki H et al. FASEB J. 2001; 15:1218-20; Luo Z, et al. Ann Thorac Surg. 1997; 64(4):993-8; Tsurui Y et al. Transplantation. 2005 May 15; 79(9):1110-5.) including the heart, brain and liver, more vulnerable to ischemia reperfusion injury initiated by other mechanisms. These include cardiac arrest (Crippen, SAS, 2005), cardiovascular shock, systemic hypotension, hypoxia, hypoxemia, hypovolemia, sleep apnea (Gozal D et al. J Neuroscience, 1 Apr. 2001, 21(7): 2442-50) transplantation surgery. (Lemasters, Annu Rev Pharmacol Toxicol, 1997, 37:327-38), TIA (Lee S-K, et al. AJNR 2004 25: 1342-7) stroke, brain trauma and chronic pressure wounds (Mustoe, Am J Surg, 2004, 187:65S-70S.) Therefore, supplemental neuroprotection may be considered in persons taking anti-VEGF treatment, especially those who have or develop a condition conducive to producing ischemia reperfusion injury.

It is well known that acute cessation of circulation may cause tissue ischemia and infarct, as occurs in retinal artery occlusion, ischemic optic neuropathy and stroke. The data herein provide evidence to support that brief intermittent ischemic episodes caused by repeated and transient circulatory compromise may culminate in tissue injury including RNFL loss, and that neuroprotective agents may be protective. Similarly, tissue injury results from the brief, intermittent ischemic episodes known as chronic intermittent hypoxia which characterize sleep apnea. Sleep apnea (without associated VEGF suppression) has been associated with reduced retinal sensitivity and RNFL loss (Ferrandez B et al., Invest Ophthalmol Vis Sci 2014; 55:71119-25; Ferrandez B et al. BMC Ophthalmol. 2016, 16:40; Zhao et al. J Glaucoma 2016; 25:e413-8) apoptosis in the brain (Xu W, et al., Neuroscience. 2004; 126(2):313-23), heart failure (Lavie L et al., Eur Respir J. 2009; 33:1467-84. Constanzo M R et al. J AM Coll Cardiol 2015; 65:72-84; Khayat R et al., Heart Fail Rev 2009; 14:143-53) and sudden cardiac death due to arrhythmia (Gami A S et al., J AM Coll Cardiol 2013; 62:610-6). The RNFL, a proxy for CNS neuronal tissue, was significantly thinner among newly diagnosed persons with sleep apnea compared to control and also demonstrated significant progressive thinning in spite of treatment with continuous positive airway pressure devices (CPAP) (Zengin M O et al., Int J Ophthalmol 2014; 7:704-8.). VEGF is elevated in sleep apnea and although it may be involved in the pathogenesis of some of its complications (Ma J et al., J Huazhong Univ Sci Technolog Med Sci 2007; 27:157-60), VEGF is a hypoxia induced neurotropic factor (Wick A et al. J Neurosci 2002; 22:6401-7; Mu D et al. Neurobiol DIs 2003; 14:524-34) that may facilitate an adaptive response to nocturnal hypoxemia (Schultz R et al., Am J Respir Crit Care Med 2002; 165:67-70; Lavie L et al., Am J Respir Crit Care Med. 2002 Jun. 15; 165(12):1624-8; Bernaudin M et al., J Cereb Blood FLow Metab 2002; 22:393-403.) and stroke (Mu D et al. Neurobiol DIs 2003; 14:524-34). Chronic VEGF inhibition during IVAV or systemic anti-VEGF administration may decrease resistance to chronic intermittent hypoxemia (Wick A et al., J Neuroscience 2002; 22:6401-7) and thereby increase risk of consequences of sleep apnea including RNFL loss and CNS neurodegenerative disorders. Therapeutic neuroprotection may be of importance for all individuals with sleep apnea including those treated with anti-VEGF agents. Further, neuroprotective compounds may prevent or ameliorate injury due to chronic intermittent hypoxia (Gozal D, et al. J Neuroscience, 2001, 21: 2442-50; Guo et al., Zhonghua Er Bi Yan Hou Tou Jing Wai Ke Za Zhi. 2016, 51:282-532; Ferrandez et al. BMC Ophthalmol. 2016, 16:40; Zhao et al. J Glaucoma 2016; 25:e413-8) and or ischemia-reperfusion injury caused by conditions including but not limited to TIA (Lee et al., AJNR 2004 25:1342-7) even among those treated with CPAP and/or in the absence of iatrogenic VEGF suppression.

Age-related decline in RNFL thickness has been reported to range from 0.16 to 0.5 um per year, and is greater in persons 50 years of age and older (Parikh et al., Ophthalmology. 2007; 114(5):921-926; Wang et al., The Beijing Eye Study 2011. PLOS One Jun. 4, 2013). While annual RNFL thinning or loss in PARA and control groups among all eyes and non-glaucomatous eyes was similar to that reported for persons over 50 years (Wang et al., The Beijing Eye Study 2011. PLOS One Jun. 4, 2013), it was 3 to 4 times greater in the corresponding non-PARA groups. Among glaucoma suspects, a 1um per year more rapid annual decline in RNFL thickness corresponded to a 2.05-times higher risk of developing a visual field defect (Miki et al., Ophthalmology. 2014. 121:1350-8). Further, RNFL thinning or loss has been associated with glaucoma associated disability and reduction in quality of life (Gracitelli et al., JAMA Ophthalmol. 2015, 133:384-90).

While annual RNFL loss in PARA and control groups among all eyes and non-glaucomatous eyes was similar to that reported for persons over 50 years (Wang et al., The Beijing Eye Study 2011. PLOS One, 2013), it was 3 to 4 times greater in the corresponding non-PARA groups. Glaucomatous eyes have an abnormal optic nerve blood-flow (Flammer et al., Prog Retin Eye Res. 1998, 17:267-89) and those with advanced disease may be more susceptible to ischemia-reperfusion injury. A statistically significant effect of paracentesis was not detected in eyes with advanced glaucoma in this study, but the number of eyes was small. Further study of this subgroup is warranted.

In summary, the results presented herein provide evidence that IOP elevations of short duration in the setting of chronic VEGF suppression may be deleterious to the RNFL, especially in eyes not being treated for glaucoma. Clinical significance may depend upon duration of an anti-VEGF therapy such as IVAV as well as comorbidities that may compromise the RNFL including advanced glaucoma and ocular or systemic disease or disorders which predispose to chronic intermittent hypoxia and/or ischemia-reperfusion injury. Future investigation of the clinical significance of our observations would be especially relevant in eyes for which the duration of treatment and total number of injections may exceed those reported or for those who have ocular or systemic comorbidities. The potential mechanism and role for neuroprotective agents in limiting RNFL thinning or loss during IVAV or other anti-VEGF therapy warrants exploration.

Example 2: Use of Tafluprost, an Anti-Pcular Hypertension Drop with Neuroprotective Properties, to Decrease RNFL Thinning or Loss and Increase the Interval Between IVAV Injections, in Eyes Treated with IVAV Intravitreal anti-VEGF injections (IVAV) are the standard of care for the treatment of choroidal neovascularization and macular edema due to a variety of disorders including macular degeneration and diabetic retinopathy, both leading causes of blindness in the western world. IVAV causes an immediate, transient elevation of intraocular pressure (IOP) which temporarily compromises intraocular circulation. VEGF suppression intended to modulate detrimental angiogenic and vasopermiability effects also chronically compromises VEGF's physiologic neuroprotective function rendering eyes more susceptible to ischemia-reperfusion injury. Multiple episodes of ischemia-reperfusion injury unmitigated by innate VEGF-derived neuroprotection may culminate in RNFL thinning or loss. Without wishing to be bound by a particular theory, it is believed that daily use of glaucoma drops with neuroprotective properties may reduce or prevent RNFL thinning or loss associated with IVAV and also increase interval between treatments.

Intravitreal injection of 0.05-0.10 ml volume transiently elevates IOP (Falkenstein et al., Retina 2007; 27:1044-7; Kim et al., Am J Ophthalmic 2008; 146:930-4; Sharei et al., Eur J Ophthalmic 2010; 20:174-9; Gismondi et al., J Glaucoma 2009; 18:658-61). IOP elevation with IVAV may reach levels that have been sufficient to compromise ocular blood flow and tissue oxygenation in animals (Shonat et al., Invest Ophthalmol Vis Sci 1992l 33:3174-80), and to cause visible central retinal arterial pulsation in humans (Nazari et al., Iranian J Ophthalmology 2009 21:13-18). The retinal artery pulsations, which indicate intraocular pressure exceed intraarterial pressure and that retinal circulation is compromised, may last from 30 seconds to 8 minutes (Nazari et al., Iranian J Ophthalmology 2009 21:13-18). IOP is highest immediately after injection. As it normalizes and retinal circulation is reestablished, in most instances within 30 minutes, the ischemia-reperfusion cycle occurs.

Data in FIG. 2 demonstrates a statistically significant difference in both maximum post injection IOP (maxIOP) and magnitude change in IOP from pre injection baseline (chgIOP) in eyes undergoing IVAV with and without adjunctive paracentesis (PARA). Higher IOP in non-PARA eyes was caused by intravitreal injection volume. PARA immediately normalized intraocular volume and consequently prevented post injection IOP rise. A statistically significant change in RNFL thinning or loss thickness (chgRNFL thinning or loss) was also detected (greater RNFL thinning or loss in nonPARA eyes) (FIG. 2). However, neither chgIOP ($r=-0.175$, p-value=0.121) nor maxIOP ($r=-0.109$, p-value=0.382) was significantly correlated with chgRNFL thinning or loss (FIG. 4). Similar results were found when using multiple linear regression accounting for age, gender, number of injections, follow-up time, baseline RNFL thinning or loss, and baseline IOP. In these models, maxIOP, chgIOP, and chgRNFL all remained significant ($p<0.0001$ for each) and final IOP remained not significant ($p=0.173$). These data suggest that elevated IOP alone is insufficient to account for the observed RNFL thinning or loss. It follows that control of the immediate post injection IOP with a single dose of anti-glaucoma medication prior to IVAV as has been suggested (Kim) would not be likely to prevent RNFL thinning or loss.

Subgroup analysis revealed that the significant decrease in RNFL thinning or loss in nonPARA eyes developed only in non-glaucomatous eyes. RNFL thinning was larger in magnitude (FIG. 2), and progressed at a statistically significantly greater rate in non-glaucomatous eyes (FIG. 3). This paradox, that eyes with glaucoma, a disease characterized by progressive RNFL thinning or loss thinning in the setting of elevated IOP, are less likely to develop RNFL thinning or loss during IVAV, may be understood upon considering the following. First, ischemia-reperfusion is an established cause of neurologic injury (Winquist and Kerr, Neurology 1997; 49 (Suppl 4) S23-6) and second, it may be mitigated by endogenous VEGF (Nisijima et al., Am J Pathol 2007; 171:53-67) or exogenous therapeutic agents which confer neuroprotectionith against ischemia-reperfusion injury.

VEGF is required for the maintenance of normal retinal ganglion cells (Nisijima et al., Am J Pathol 2007; 171:53-67) and inhibition of VEGF's maintenance effect has the potential to cause RNFL injury. Further, VEGF normally protects against ischemia-reperfusion injury (Nisijima et al., Am J Pathol 2007; 171:53-67). The data in FIG. 2 shows that chgRNFL thinning or loss in eyes treated with anti-VEGF agents plus paracentesis did not differ from that observed in fellow eye controls. This suggests VEGF inhibition itself does not account for the significant difference in chgRNFL thinning or loss we observed between PARA and non-PARA groups. Taken as a whole, the data in the tables suggest RNFL thinning or loss required that two factors were present, that is, it developed in eyes exposed to repeated episodes of ischemia-reperfusion while they were also vulnerable to ischemic injury owing to compromised innate neuroprotiction during in a state of deficient innate chronic iatrogenic VEGF suppression.

Glaucoma drops are administered to control elevated IOP. Some also have demonstrable neuroprotective properties. For example, in animals, tafluprost protects retinal gangion cells from apoptosis both in vitro and in vivo (Kanamori et al., Graefes Arch Clin Exp Ophthalmol 2009; 247:1353-60). Further, prostaglandin F2α analogues including tafluprost improved optic nerve blood flow in animal models (Kurishima et al., Exp Eye Res 2010; 91:853-9). Daily topical administration of tafluprost was also shown to be protective against endothelin 1 induced ischemic retinal injury in animals. RNFL thinning or loss was thicker in treated eyes (Nagata et al., Invest Ophthalmol Vis Sci 2014 55:1040-7). These animal studies of ischemic injury to the optic nerve and retina demonstrate neuroprotective properties of glaucoma medications in the setting of ischemia, and may be relevant to ischemia-reperfusion injury associated with IVAV.

Among non-glaucomatous eyes there was a statistically significant difference in chgRNFL thinning or loss between PARA and nonPARA eyes. This suggests non-glaucomatous nonPARA eyes subject to elevated IOP and repeated ischemia-reperfusion episodes in the setting of reduced or absent innate VEGF suffered loss of RNFL thinning or loss. In contrast, no significant difference in chgRNFL thinning or loss between PARA and non-PARA eyes was detected in the glaucoma eye subgroup (eyes using daily glaucoma drops) (FIG. 2) and RNFL thinning or loss was similar in treatment eyes and controls. These data support the hypothesis that glaucoma drops used on a daily basis during IVAV provided pharmacologic neuroprotection against ischemia-reperfusion injury. This pharmacologic protection prevented statistically significant RNFL thinning or loss in non-PARA eyes.

There is a second potential beneficial effect of daily use of the prostaglandin F2α analogue tafluprost during the course of IVAV. The neuroprotective effect of tafluprost is mediated by inhibition of endothelin 1 (Nagata et al., Invest Ophthalmol Vis Sci 2014 55:1040-7). Down-regulation of endothelin 1, a stimulator of VEGF expression, decreases VEGF mRNA production (Tsuda et al., J Glaucoma 2013; 22:389-403). It follows that daily use may also decrease intraocular VEGF concentration, and thereby potentiate anti-VEGF agents used in IVAV. Daily topical use may be expected to increase interval between anti-VEGF injections and therefore decrease the number and frequency of anti-VEGF injections required per patient in a treat and extend protocol compared to control. Sustained IOP elevation is related to number of injections (Abedi et al., Semin Ophthamol, 2013, 28:126-130; Singh and Kim, Drugs Aging, 2012, 28:949-956).

The annual RNFL thinning or loss reported herein was 3 to 4 times greater in the non-glaucomatous non-PARA eyes than that normally attributed to aging (Parikh et al., Ophthalmology. 2007; 114(5):921-6; Wang et al., PLOS One, 2013, 0066763). In a study of glaucoma suspects, a 1 um per year more rapid annual decline in RNFL thinning or loss corresponded to a 2.05-times higher risk of developing a visual field defect (Miki et al., Ophthalmology. 2014; 121 (7):1350-8). Further, RNFL thinning or loss has been associated with glaucoma associated disability and reduction in quality of life (Gracitelli et al., JAMA Ophthalmol. 2015; 133(4):384-90). The clinical significance of IVAV associated RNFL thinning or loss thinning may depend upon additional factors. Susceptibility to ischemia is related to ocular perfusion which may be compromised by systemic vascular factors including diabetes (Panes et al., Circulation 1996; 13: 161-7), hypertension and anti-hypertensive medications (Deb et al., Indian J Ophthalmol. 2014; 62(9):917-22; Wang et al., Curr Eye Res. 2014; 9:1-9; Yip et al., Invest Ophthalmol Vis Sci. 2011; 52(11):8186-92). It would seem prudent therefore to take measures to minimize RNFL thinning or loss thinning, especially in persons with systemic vascular disease, in those who are younger or whose duration of treatment and total number of injections is expected to be greater.

Without wishing to be bound by a particular theory, it is believed that tafluprost may decrease or prevent RNFL thinning that develops during IVAV when adjunctive paracentesis is not performed, and that treatment with tafluprost will allow an increase the interval between anti-VEGF injections and therefore result in a decreased number and/or frequency of anti-VEGF injections per subject in a treat and extend protocol compared to control.

To demonstrate tafluprost decreases RNFL thinning in eyes without glaucoma that are being treated with IVAV, and that treatment with tafluprost can further increase the interval of time between multiple IVAV procedures and/or reduce the number of IVAV procedures necessary for an effective IVAV treatment regimen, intraviteal injections are performed according to a treat and extend protocol (Spaide, Am J Ophthalmol. 2007, 143:679-80; Engelbert et al., Retina, 2010, 30:1368-75; Engelbert et al., Retina, 2009, 29:1424-31) in three groups. The one treatment group (Groups 1) receives tafluprost (below), while the control group (Group 2) receives placebo (artificial tears). Group 1: Tafluprost 0.0015% one drop once a day at bedtime for the duration of IVAV. Group 2: Control, placebo (preservative free artificial tears) one drop once a day at bedtime for the duration of IVAV.

To determine if treatment with tafluprost increases the interval between intravitreal anti-VEGF injections and thereby decreases the number of injections required in a treat and extend protocol, total number of injections/year and intervals between injections are compared between the treatment groups and the measures of change in RNFL thickness, rate of change in RNFL thickness, number of injections per year, intraocular pressure, and visual acuity are determined. Adverse events that are monitored include endophthalmitis, anterior segment injury (hyphema, lens injury) and pre-injection IOP>25 mm hg.

Baseline refraction is performed. Ophthalmic photographers obtained sd-OCT (Spectralis, Heidelberg Engineering) prior to each injection and scanned images into the electronic medical record. RNFL thickness calculated by the autosegmentation algorithm including mean central, inferior, superior, nasal and temporal thickness is recorded. Intraocular pressure is obtained using tonopen (Reichert Technologies) before and immediately and 10 minutes after injection. Tonopen is used in lieu of applanation in order to facilitate immediate post-injection IOP measurement. If the 10-minute post injection IOP was greater than 30 mm hg, additional IOP readings were obtained at 10 minute intervals until IOP was 30 mm hg or less.

Intravitreal injections are administered through 30 gauge needles through the pars plana in either the superotemporal or inferotemporal quadrant according to physician preference. A cotton tipped applicator was placed over the injection site. One of three anti-VEGF medications (ranibizumab, bevacizumab, aflibercept) chosen at the discretion of the treating physician is administered in 0.05 ml volume. Anesthesia is chosen based on subject and physician preference, and methods may include topical proparacaine or tetracaine drops, 2% lidocaine gel or subconjunctival injection of 2% lidocaine solution. Standard pre-injection sterilization will include eyelid prep using 10% betadine swab and additional betadine instilled into the conjunctiva. Betadine is applied to the conjunctiva using a 10% betadine swab immediately prior to injection. Following injection, all eyes are irrigated with balanced salt solution.

The methods and materials are now described.

Treat and Extend Protocol

Subjects are injected with intravitreal anti-VEGF once a month for three months. Once stability is achieved with monthly dosing, (stable visual acuity, an absence of macular hemorrhage, and a dry OCT) the subject is instructed to return in six weeks. Visual acuity, clinical findings, and OCT changes are recorded again and subjects receive an injection. The interval to the next visit with scheduled injection is based on an observed change in the above parameters. If there are no changes, the interval to the next visit is extended to seven weeks with scheduled injection. However, if there is evidence of disease reactivation, the interval for the next scheduled injection and examination is shortened by one week.

Topical Medication

Group 1 subjects will use tafluprost once daily at bedtime throughout the course of therapy. The control group (group 2) will receive preservative free artificial tears once daily at bedtime throughout the course of therapy.

Statistical Analysis

Sample size was determined as a balance of statistical power and feasibility of recruitment. To evaluate sample size, the size of detectable standard deviation unit (SDU) was used. The SDU corresponds to a beta coefficient in a regression model when we assume the standard normal deviate (i.e. N(0,1)). A sample size of 65 per group (130 total) will have 80% power to detect an SDU of 0.50 (a moderate effect size). An SDU of 0.50 corresponds to an absolute difference equal to half the size of the standard deviation that translates into a 13% shift in a standard normal distribution.

Data is summarized using means with standard deviations (continuous data) or percentages (categorical data). Baseline characteristics (age, gender, refractive error, IOP and mean central RNFL) (Alasil et al., J Glaucoma 2013, 22:532-41) are compared between the groups using analysis of variance (ANOVA) or Chi-square test, as appropriate. Post injection outcomes are evaluated by comparing change in IOP from baseline to final IOP, change in RNFL thinning or loss and rate of change in RNFL thinning or loss between the treatment groups using ANOVA. Pearson's correlation coefficient is used to measure the extent of correlation between the IOP outcomes, change in RNFL thinning or loss and rate change in RNFL thinning or loss. SAS version 9.3 is used for statistical analysis, all tests are two-sided, and p-values<0.05 are considered significant. Multiple linear regression adjusting for age, gender, refractive error, number of injections, follow-up time, baseline RNFL thinning or loss, and baseline IOP are used to determine if differences between groups remained after accounting for potential biases.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of protecting against retinal nerve fiber thinning or loss and ischemia-reperfusion injury associated with intravitreal anti-VEGF injection (IVAV) treatment in a subject in need thereof, said method comprising administering an effective amount of a composition comprising a prostaglandin analog to the subject, wherein the subject is a human subject not receiving a neuroprotective prostaglandin analog for the treatment of glaucoma, and wherein the subject will experience or has experienced IVAV, wherein said prostaglandin analog is tafluprost.

2. The method of claim 1 wherein said composition is capable of crossing the blood-brain barrier and the blood-retina barrier.

3. The method of claim 1, wherein said composition is administered to said subject by way of an administration route selected from the group consisting of topical, oral, intravenous, periocular injection and an intraocular implant drug delivery device.

4. The method of claim 1, wherein said composition is administered to said subject daily for at least three months.

5. The method of claim 1, wherein said composition is administered to said subject by way of one or more treatment regimen selected from the group consisting of at least once prior to IVAV treatment and at least once following IVAV treatment.

6. The method of claim 1, wherein said composition is administered to said subject daily for the duration and for at least three months following an IVAV treatment regimen.

7. The method of claim 6, whereby one or more of the time interval between IVAV injections is increased and the number of IVAV injections is decreased relative to the average time interval and number of injections received respectively by control individuals.

8. The method of claim 1 comprising the steps of:
   a) administering an effective amount of tafluprost to the subject; and
   b) administering an intravitreal anti-VEGF injection (IVAV) treatment to the subject.

9. The method of claim 8, wherein step a) and step b) are performed in a manner selected from the group consisting of: step a) is performed prior to step b), step b) is performed prior to step a), and step a) is performed concurrently with step b).

* * * * *